United States Patent [19]

Van Leeuwen et al.

[11] Patent Number: 5,066,777
[45] Date of Patent: Nov. 19, 1991

[54] POLYMERIZATION OF CO/OLEFIN WITH DIPHOSPHINE/HYDROCARBYL PALLADIUM SALT COMPLEX CATALYST

[75] Inventors: Petrus W. N. M. Van Leeuwen; Cornelis F. Roobeek, both of Amsterdam, Netherlands; Pui K. Wong, Katy, Tex.

[73] Assignee: Shell Oil Company, Houston, Tex.

[21] Appl. No.: 474,959

[22] Filed: Feb. 5, 1990

[30] Foreign Application Priority Data

Mar. 15, 1989 [NL] Netherlands ................. 8900629

[51] Int. Cl.$^5$ .................................... C08G 67/02
[52] U.S. Cl. .................................... 528/392; 502/162
[58] Field of Search .................................... 528/392

[56] References Cited

U.S. PATENT DOCUMENTS 3,694,412  9/1972  Nozaki ..................... 260/63 CQ

FOREIGN PATENT DOCUMENTS 121965  10/1984  European Pat. Off. .
257663   3/1988  European Pat. Off. .

Primary Examiner—Harold D. Anderson

[57] ABSTRACT

An improved process for the production of linear alternating polymer of carbon monoxide and at least one ethylenically unsaturated hydrocarbon comprises the use as a catalyst composition of a novel complex containing a diphosphine/hydrocarbylpalladium cation and an anion of a non-hydrohalogenic acid having a pKa below 2. The polymers are useful as engineering thermoplastics.

9 Claims, No Drawings

POLYMERIZATION OF CO/OLEFIN WITH DIPHOSPHINE/HYDROCARBYL PALLADIUM SALT COMPLEX CATALYST

FIELD OF THE INVENTION

The present invention relates to an improved process for the production of linear alternating polymer of carbon monoxide and at least one ethylenically unsaturated hydrocarbon. More particularly, the present invention relates to a process for the production of such linear alternating polymers in the presence of novel catalyst compositions comprising a complex of diphosphine/hydrocarbylpalladium cation and the anion of a non-hydrohalogenic acid having a pKa below 2.

BACKGROUND OF THE INVENTION

The class of polymers of carbon monoxide and olefin(s) has been known for some time. Brubaker, U.S. Pat. No. 2,495,286, produced such polymers of relatively low carbon monoxide content in the presence of free radical initiators, e.g., peroxy compounds. G.B. 1,081,304 produced similar polymers of higher carbon monoxide content in the presence of alkylphosphine complexes of palladium salts as catalyst. Nozaki extended the reaction to produce linear alternating polymers in the presence of arylphosphine complexes of palladium moieties and certain inert solvents. See, for example, U.S. Pat. No. 3,694,412.

More recently, the class of linear alternating polymers of carbon monoxide and at least one ethylenically unsaturated hydrocarbon has become of greater interest in part because of the greater availability of the polymers. The more recent processes for the production of the linear alternating polymers, now known as polyketones or polyketone polymers, are illustrated by a number of published European Patent Applications including 121,965, 181,014, 213,671 and 257,663. The processes generally involve the use of a catalyst composition formed from a compound of palladium, cobalt or nickel, the anion of a strong non-hydrohalogenic acid and a bidentate ligand of phosphorous, arsenic or antimony. Without wishing to be limited, preferred catalyst compositions are formed from a compound of palladium, the anion of a non-hydrohalogenic acid having a pKa below 2 and a bidentate ligand of phosphorus.

Even more recently, catalyst compositions have been employed which include diphosphine complexes of a hydrocarbylpalladium halide salt. In copending U.S. patent application Ser. No. 433,871, filed Nov. 9, 1989, the use of a diphosphine/hydrocarbylpalladium halide complex is disclosed as a catalyst composition for the production of the linear alternating polymers. Although such complexes give good results when employed as the catalyst composition, it would be of advantage to provide additional catalyst compositions useful in the preparation of linear alternating polymers of carbon monoxide and at least one ethylenically unsaturated hydrocarbon.

SUMMARY OF THE INVENTION

The present invention provides an improved process for the production of linear alternating polymers of carbon monoxide and at least one ethylenically unsaturated hydrocarbon. More particularly, the invention provides a process for the production of the linear alternating polymers which employs, as a catalyst composition, a novel complex of a diphosphine/hydrocarbylpalladium cation and the anion of a non-hydrohalogenic acid having a pKa below 2.

DESCRIPTION OF THE INVENTION

The ethylenically unsaturated hydrocarbons which are employed as precursors of the linear alternating polymers have up to 20 carbon atoms inclusive, preferably up to 10 carbon atoms inclusive, and are aliphatic such as ethylene and other $\alpha$-olefins including propylene, 1-butene, isobutylene, 1-hexene, 1-octene and 1-dodecene or are arylaliphatic containing an aryl substituent on an otherwise aliphatic molecule, particularly an aromatic substituent on a carbon atom of the ethylenic unsaturation. Illustrative of this latter class of ethylenically unsaturated olefins are styrene, p-methylstyrene, p-ethylstyrene and m-isopropylstyrene. The preferred polyketone polymers are copolymers of carbon monoxide and ethylene or terpolymers of carbon monoxide, ethylene and a second ethylenically unsaturated hydrocarbon of at least 3 carbon atoms, particularly an $\alpha$-olefin such as propylene.

The structure of the polyketone polymers is that of a linear alternating polymer and the polymer will contain substantially one molecule of carbon monoxide for each molecule of ethylenically unsaturated hydrocarbon. When the preferred terpolymers are produced according to the process of the invention there will be at least about 2 units incorporating a moiety of ethylene for each unit incorporating a moiety of the second hydrocarbon. Preferably, there will be from about 10 units to about 100 units incorporating a moiety of ethylene for each unit incorporating a moiety of the second hydrocarbon. The polymer chain of the preferred polyketone polymers is therefore represented by the repeating formula $$\pm CO\pm CH_2\pm CH_2)]_x[CO\pm G)]_y \qquad (I)$$

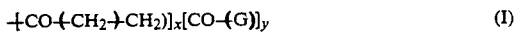

wherein G is the moiety of an ethylenically unsaturated hydrocarbon polymerized through the ethylenic unsaturation thereof and the ratio of y:x is no more than about 0.5. When the preferred copolymers are produced by the process of the invention there will be no second hydrocarbon present and the copolymers are represented by the above formula I wherein y is zero. When y is other than zero, i.e., terpolymers are produced, the $-CO+CH_2CH_2\}-$ units and the $-CO+G\}-$ units are found randomly throughout the polymer chain and the preferred ratio of y:x is from about 0.01 to about 0.1. The end groups or "caps" of the polymer chain will depend upon what materials are present during the production of the polyketone and how and whether the polymer has been purified. However, the properties of the polymer will not depend to any considerable extent upon the precise nature of the end groups so that the polymers are fairly depicted by the formula for the polymeric chain as depicted above.

Of particular interest are the polyketone polymers of number average molecular weight from about 1000 to about 200,000, particularly those polymers of number average molecular weight from about 20,000 to about 90,000, as determined by gel permeation chromatography. The physical properties of the polymers will depend in part on the molecular weight of the polymer, whether the polymer is a copolymer or a terpolymer and, in the case of terpolymers, the nature of and the proportion of the second hydrocarbon present. Typical melting points of the polymers are from about 175° C. to about 300° C., more frequently from about 210° C. to about 270° C. The polymers will have a limiting viscosity number, measured in a standard capillary viscosity measuring device in m-cresol at 60° C., of from about 0.5 dl/g to about 10 dl/g, preferably from about 0.8 dl/g to about 4 dl/g.

The process of the invention comprises contacting the carbon monoxide and hydrocarbon monomers and the catalyst complex in the presence of a reaction diluent, under polymerization conditions. The catalyst complex to be employed is a diphosphine/hydrocarbylpalladium cation and an anion of a non-hydrohalogenic acid having a pKa below 2. The diphosphine component of the catalyst complex is a tetraaryldiphosphine component wherein each aryl moiety has up to 10 carbon atoms and is hydrocarbyl containing only atoms of carbon and hydrogen or is substituted hydrocarbyl containing additional atoms in the form of monovalent aromatic ring substituents which are preferably polar and substituted on an aromatic ring carbon which is ortho to the carbon atom through which the aryl group is connected to a phosphorus. A preferred class of tetraaryldiphosphines is represented by the formula

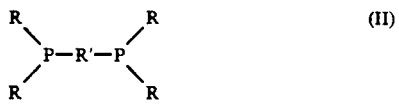

wherein R independently is aryl of up to 10 carbon atoms inclusive and R' is a bridging group of from 2 to 8 carbon atoms inclusive with from 2 to 4 carbon atoms in the bridge connecting the two phosphorus atoms. Illustrative R' groups include 1,2-ethylene, 1,3-propylene, 1,4-butylene, 1,3-butylene and 2,2-dimethyl-1,3-propylene. Of these, the 1,3-propylene or trimethylene group is preferred. A preferred class of R substituents comprises phenyl and alkoxyphenyl including 2-methoxyphenyl, 2,6-dimethoxyphenyl, 2,4,6-trimethoxyphenyl, 2-propoxyphenyl and 2,4-diethoxyphenyl. The diphosphines 1,3-bis(diphenylphosphino)propane and 1,3-bis[di(2-methoxyphenyl)phosphino]propane are preferred as the diphosphine component of the catalyst complex. The hydrocarbyl portion of the diphosphine/hydrocarbylpalladium is a monovalent aliphatic unsubstituted hydrocarbyl or substituted hydrocarbyl substituent of up to 10 carbon atoms inclusive. The group is saturated containing only single carbon-carbon bonds or is unsaturated containing multiple bonds between adjacent carbon atoms. Illustrative of such hydrocarbyl groups are saturated hydrocarbyl groups, i.e., alkyl groups, such as methyl, ethyl, butyl (3-methoxytricyclo[2.2.1.0]heptyl-5) and hexyl, and unsaturated hydrocarbyl groups such as allyl, methallyl and crotyl groups. The anion ]heptyl-5) groups. The anion of the catalyst complexes of the invention is the anion of a non-hydrohalogenic acid having a pKa below 2 (measured in water at 18° C.). Suitable acids are inorganic acids such as sulfuric acid or perchloric acid or are organic acids including carboxylic acids such as trichloroacetic acid, trifluoroacetic acid and dichloroacetic acid as well as sulfonic acids such as methanesulfonic acid and trifluoromethanesulfonic acid. The anion of trifluoroacetic acid and p-toluenesulfonic acid constitute a preferred class of anions.

The catalyst complexes employed in the present invention are produced in two synthetic steps from the corresponding diphosphine complex of a palladium dihalide, particularly palladium dichloride. In a first step, the diphosphine/palladium dihalide is reacted with a tetra(hydrocarbyl)tin to produce the diphosphine/hydrocarbylpalladium complex. By way of specific illustration, a diphosphine/palladium dichloride complex is reacted with tetramethyltin to produce the diphosphine/methylpalladium chloride complex. This intermediate complex is reacted with the silver salt of the non-hydrohalogenic acid whose anion is desired in the catalyst complex. By way of illustration, a diphosphine/methylpalladium chloride is reacted with silver p-toluenesulfonate to produce by-product silver chloride and the desired diphosphine/methylpalladium p-toluenesulfonate. These reactions are typically conducted in an inert reaction solvent such as dichloromethane. The overall synthesis is by known methods.

The polymerization is conducted in the presence of a reaction diluent under polymerization conditions. Reaction diluents that are useful are inert reaction diluents including alcohols such as methanol and ethanol, ethers, especially cyclic ethers such as tetrahydrofuran and dioxane, hydrocarbons such as benzene and toluene and halohydrocarbons such as chlorobenzene and dichloromethane. Mixtures of diluents are also suitable. Typical polymerization conditions include a reaction temperature below about 150° C. and preferably from about 20° C. to about 100° C. The polymerization pressure is from about 2 bar to about 150 bar, although pressures from about 5 bar to about 100 bar are more common. The molar ratio of carbon monoxide to hydrocarbon to be polymerized is from about 10:1 to about 1:10 but preferably is from about 5:1 to about 1:5. The catalyst complex is employed in a catalytic quantity. Amounts of catalyst complex sufficient to provide from about $1 \times 10^{-7}$ mol to about $1 \times 10^{-3}$ mol of palladium per mol of hydrocarbon to be polymerized are useful with amounts of catalyst complex sufficient to provide from about $1 \times 10^{-6}$ mol to about $1 \times 10^{-4}$ mol of palladium per mol of hydrocarbon being preferred.

The contacting of the carbon monoxide and hydrocarbon reactants, the catalyst complex and the reaction diluent is conducted in a suitable reactor and reactant/catalyst contacting is facilitated by some means of agitation such as shaking or stirring. Subsequent to polymerization the reaction is terminated as by cooling the reactor and releasing the pressure. The polymer product is typically obtained as a product substantially insoluble in the media of its production and is recovered by conventional procedures such as filtration or decantation. The polyketone polymer is used as recovered or alternatively is purified as by contacting the polymer with a solvent or complexing agent selective for catalyst residues.

The polyketone product of the process of the invention is a thermoplastic polymer of relatively high melting point and has demonstrated utility as an engineering thermoplastic. The polymers are processable by methods conventional for the processing of thermoplastic polymers such as injection molding, extrusion and thermoforming into a variety of shaped articles exhibiting dimensional stability at elevated temperatures. Specific applications include the production of containers for food and drink and the production of housings and parts for automotive applications.

The invention is further illustrated by the following Comparative Example (not of the invention) and the following Illustrative Embodiments which should not be regarded as limiting.

ILLUSTRATIVE EMBODIMENT I

To a solution of 0.1 mmol of [2,2-dimethyl-1,3-bis(diphenylphosphino)propane]methylpalladium chloride in a mixture of 0.5 ml of dichloromethane and 0.5 ml methanol was added 0.1 mmol of silver trifluoromethanesulfonate. After stirring for 5 minutes at room temperature, the precipitated silver chloride was removed by filtration and the solvent was removed by evaporation from the filtrate. A yield of 0.07 g of [2,2-dimethyl-1,3-bis(diphenylphosphino)propane]methylpalladium trifluoromethanesulfonate was obtained.

ILLUSTRATIVE EMBODIMENT II

To a suspension of 1.4 g of {1,3-bis[di(2-methoxyphenyl)phosphino]propane}palladium dichloride in a mixture of 10 ml of dichloromethane and 10 ml of methanol was added 0.72 g of tetramethyltin. The resulting mixture was stirred for 2 hours at room temperature and the solvents were removed in vacuo from the mixture. The residue was washed twice with 5 ml portions of diethyl ether and dissolved in 15 ml of dichloromethane. To the solution thus obtained was added 0.5 g of silver trifluoromethanesulfonate in 5 ml of methanol. The precipitated silver chloride was removed by filtration and the solvents were removed by evaporation. The residue was washed with 4 ml of methanol and dried. A yield of 1.6 g of {1,3-bis[di(2-methoxyphenyl)phosphino]propane}methylpalladium trifluoromethanesulfonate was obtained.

ILLUSTRATIVE EMBODIMENT III

To a solution of 1.0 g of the dimer of {6-methoxybicyclo[2.2.1]-heptene-2-yl}palladium chloride in 25 ml of dichloromethane was added 2.01 g of 1,3-bis[di(2-methoxyphenyl)phosphino]propane. After the resulting mixture was stirred for 15 minutes at room temperature, 1.06 g of silver p-toluenesulfonate was added. After an additional 15 minutes of stirring, the precipitated silver chloride was removed by filtration. Pentane was added to the filtrate and the resulting precipitate was recovered by filtration and dried. A yield of 3.7 g of {1,3-bis[di(2-methoxyphenyl)phosphino]propane}{3-methoxytricyclo[2.2.1.0]heptyl-5}palladium p-toluenesulfonate was obtained.

ILLUSTRATIVE EMBODIMENT IV

The procedure of Illustrative Embodiment III was substantially repeated except that 0.84 g of silver trifluoroacetate was added instead of the silver p-toluenesulfonate. A 2.0 g yield of {1,3-bis[di(2-methoxyphenyl)phosphino]propane}{3-methoxytricyclo[2.2.1.0]heptyl-5}palladium trifluoroacetate was obtained.

ILLUSTRATIVE EMBODIMENT V

The procedure of Illustrative Embodiment IV was substantially repeated except that 1.56 g of 1,3-bis(diphenylphosphino)propane was used rather than the 1,3-bis[di(2-methoxyphenyl)phosphino]propane. A yield of 2.0 g of [1,3-bis(diphenylphosphino)propane]{3-methoxytricyclo[2.2.1.0]-heptyl-5}palladium trifluoroacetate was obtained.

ILLUSTRATIVE EMBODIMENT VI

The procedure of Illustrative Embodiment III was substantially repeated except that 1.56 g of 1,3-bis(diphenylphosphino)propane was employed instead of the 1,3-bis[di(2-methoxyphenyl)phosphino]propane. A yield of 2.8 g of [1,3-bis(diphenylphosphino)propane]{3-methoxytricyclo[2.2.1.0]heptyl-5}palladium p-toluenesulfonate was obtained.

ILLUSTRATIVE EMBODIMENT VII

To a solution of 18.3 mg of the dimer of allylpalladium chloride in 5 ml of dichloromethane were consecutively added 53.2 mg of 1,3-bis[di(2-methoxyphenyl)phosphino]propane and 27.9 g of silver p-toluenesulfonate. After the solution was stirred for 15 minutes, the precipitated silver chloride was removed by filtration. The filtrate contained {1,3-bis[di(2-methoxyphenyl)phosphino]propane}allylpalladium p-toluenesulfonate.

COMPARATIVE EXAMPLE

A copolymer of carbon monoxide and ethylene was produced by charging to an autoclave of 250 ml capacity equipped with a stirrer a catalyst composition solution containing 100 ml of methanol and 0.1 mmol of [2,2-dimethyl-1,3-bis(diphenylphosphino)propane]methylpalladium chloride. The air present in the autoclave was removed by evacuation and an equimolar mixture of carbon monoxide and ethylene was added until a pressure of 40 bar had been reached. After 4 hours of stirring at room temperature the polymerization was terminated by releasing the pressure. The copolymer product was recovered by filtration, washed with methanol and dried. The yield of copolymer was 1.5 g, obtained at a rate of 35 g of copolymer/g Pd hr.

ILLUSTRATIVE EMBODIMENT VIII

The procedure of the Comparative Example was substantially repeated except that the catalyst composition comprised 0.1 mmol of the complex [2,2-dimethyl-1,3-bis(diphenylphosphino)propane]methylpalladium trifluoromethane sulfonate produced according to Illustrative Example I and the reaction time was 1 hour instead of 4 hours. The yield of copolymer was 3.4 g, produced at a rate of 317 g of copolymer/g Pd hr.

ILLUSTRATIVE EMBODIMENT IX

A copolymer of carbon monoxide and ethylene was produced by a procedure substantially similar to that of Illustrative Embodiment VIII except that the catalyst composition solution contained 100 ml of toluene instead of methanol and the reaction time was 2 hours instead of 1 hour. The yield of copolymer was 2.4 g, produced at a rate of 112 g of copolymer/g Pd hr.

ILLUSTRATIVE EMBODIMENT X

A copolymer of carbon monoxide and ethylene was produced by a procedure substantially similar to that of Illustrative Embodiment VIII except that the catalyst composition contained 100 ml of diethyl ether instead of methanol and the reaction time was 2 hours instead of 1 hour. The yield of copolymer was 1.2 g, produced at a rate of 56 g of copolymer/g Pd hr.

ILLUSTRATIVE EMBODIMENT XI

A copolymer of carbon monoxide and ethylene was produced by charging to an autoclave of 250 ml capacity equipped with a mechanical stirrer a catalyst composition solution comprising 100 ml of methanol and 0.05 mmol of the complex {1,3-bis[di(2-methoxyphenyl)-phosphino]propane}-methylpalladium trifluoromethanesulfonate prepared according to Illustrative Embodiment II. After the air present in the autoclave was removed by evacuation, an equimolar mixture of carbon monoxide and ethylene was added until a pressure of 50 bar was reached. The contents of the autoclave were warmed to 85° C. and maintained at that temperature for 20 minutes. Polymerization was then terminated by cooling to room temperature and releasing the pressure. The copolymer product was recovered by filtration, washed with methanol and dried. The yield of copolymer was 7.5 g, produced at a rate of 4.2 kg of copolymer/g Pd hr.

ILLUSTRATIVE EMBODIMENT XII

A carbon monoxide/ethylene copolymer was produced by a procedure substantially similar to that of Illustrative Embodiment XI except that the catalyst composition solution contained 100 ml of toluene instead of methanol and the reaction time was 45 minutes instead of 20 minutes. The yield of copolymer was 7.0 g, produced at a rate of 1.7 kg of copolymer/g Pd hr.

ILLUSTRATIVE EMBODIMENT XIII

A copolymer of carbon monoxide and ethylene was produced by a procedure substantially similar to that of Illustrative Embodiment XI except that the catalyst composition contained 100 ml of dichloromethane instead of methanol, the reaction temperature was 80° C. instead of 85° C. and the reaction time was 30 minutes instead of 20 minutes. The yield of copolymer was 4.0 g, produced at a rate of 1.5 kg of copolymer/g Pd hr.

ILLUSTRATIVE EMBODIMENT XIV

A copolymer of carbon monoxide and ethylene was produced by a procedure substantially similar to that of Illustrative Embodiment XI except that the catalyst composition solution contained 100 ml of tetrahydrofuran instead of methanol, the reaction temperature was 90° C. instead of 85° C. and the reaction time was 30 minutes instead of 20 minutes. The yield of copolymer was 8.5 g, produced at a rate of 3.2 kg of copolymer/g Pd hr.

ILLUSTRATIVE EMBODIMENT XV

A copolymer of carbon monoxide and ethylene was produced by charging 220 ml of methanol to an autoclave of 300 ml capacity equipped with a mechanical stirrer. After the contents of the autoclave were heated to 90° C., an equimolar mixture of carbon monoxide and ethylene was added until a pressure of 55 bar was reached. The autoclave was then charged with a catalyst composition solution comprising 0.01 mmol of a palladium p-toluenesulfonate complex prepared by the procedure of Illustrative Embodiment III in 10 ml of methanol. The resulting polymerization was terminated after 3.5 hours by cooling the autoclave and contents to room temperature and releasing the pressure. The copolymer product was recovered by filtration, washed with methanol and dried. The yield of copolymer was 6.0 g, produced at a rate of 1.67 kg of copolymer/g Pd hr.

ILLUSTRATIVE EMBODIMENT XVI

A carbon monoxide/ethylene copolymer was produced by a procedure substantially similar to that of Illustrative Embodiment XV except that the catalyst composition solution comprised 0.01 mmol of a palladium trifluoroacetate complex produced according to Illustrative Embodiment IV instead of the palladium p-toluenesulfonate complex and the reaction time was 2.47 hours instead of 3.5 hours. The yield of copolymer was 7.47 g, produced at a rate of 2.9 kg of copolymer/g Pd hr.

ILLUSTRATIVE EMBODIMENT XVII

A copolymer of carbon monoxide and ethylene was produced by a procedure substantially similar to that of Illustrative Embodiment XV except that the autoclave was initially charged with 220 ml of chlorobenzene instead of methanol. The catalyst composition solution comprised 0.047 mmol of the palladium complex instead of 0.01 mmol and 20 ml of chlorobenzene instead of methanol, and the reaction time was 6.73 hours instead of 3.5 hours. The yield of copolymer was 19.83 g, produced at a rate of 0.59 kg of copolymer/g Pd hr.

ILLUSTRATIVE EMBODIMENT XVIII

A carbon monoxide/ethylene copolymer was produced by charging to an autoclave of 300 ml capacity equipped with a stirrer 75 ml of methanol and 108 g of 1,4-benzoquinone. The solution of the palladium p-toluenesulfonate complex of Illustrative Embodiment VII in dichloromethane was added. Carbon monoxide was introduced until a pressure of 30 bar had been reached and ethylene was added until a total pressure of 60 bar was reached. The contents of the autoclave were heated to 90° C. and maintained at that temperature for 9 hours. Polymerization was then terminated by cooling the autoclave and contents to room temperature and releasing the pressure. The polymer product was recovered by filtration, washed with methanol and dried. The yield of copolymer was 11.7 g, produced at a rate of 130 g of copolymer/g Pd hr.

PRODUCT ANALYSIS

The copolymeric products produced by the Comparative Example and Illustrative Embodiments VIII-XVIII were examined by $^{13}$C-NMR. The spectra were consistent with a linear polymer of alternating carbon monoxide and ethylene moieties.

What is claimed is:

1. In the process for the production of linear alternating polymers of carbon monoxide and at least one ethylenically unsaturated hydrocarbon by contacting the carbon monoxide and hydrocarbon under polymerization conditions in the presence of a reaction diluent and a catalytic quantity of a diphosphine/hydrocarbylpalladium salt complex, the improvement wherein the complex comprises a tetraaryldiphosphine/hydrocarbylpalladium cation and the anion of a non-hydrohalogenic acid having a pKa below 2.

2. The process of claim 1 wherein the hydrocarbyl moiety is unsubstituted hydrocarbyl or substituted hydrocarbyl of up to 10 carbon atoms inclusive.

3. The process of claim 2 wherein the disphosphine is represented by the formula

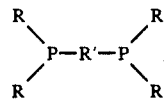

wherein R independently is aryl of up to 10 carbon atoms inclusive and R' is a bridging group of from 2 to 8 carbon atoms inclusive with from 2 to 4 carbon atoms in the bridge.

4. The process of claim 4 wherein R is phenyl or 2-methoxyphenyl.

5. The process of claim 4 wherein R' is 1,3-propylene.

6. The process of claim 5 wherein the anion is the anion of trifluoroacetic acid or p-toluenesulfonic acid.

7. The process of claim 6 wherein the hydrocarbyl moiety is methyl or allyl.

8. The process of claim 7 wherein R is 2-methoxyphenyl.

9. The process of claim 8 wherein the hydrocarbyl moiety is methyl.

* * * * *